(12) United States Patent
Toral Bardina

(10) Patent No.: US 11,219,291 B2
(45) Date of Patent: Jan. 11, 2022

(54) FALSE NAIL AND METHOD FOR SHAPING SAME ON A NATURAL NAIL

(71) Applicant: Manuel Enrique Toral Bardina, Ciutadella de Menorca (ES)

(72) Inventor: Manuel Enrique Toral Bardina, Ciutadella de Menorca (ES)

( * ) Notice: Subject to any disclaimer, the term of this patent is extended or adjusted under 35 U.S.C. 154(b) by 99 days.

(21) Appl. No.: 16/467,916

(22) PCT Filed: Dec. 11, 2017

(86) PCT No.: PCT/ES2017/070805
§ 371 (c)(1),
(2) Date: Jun. 7, 2019

(87) PCT Pub. No.: WO2018/104574
PCT Pub. Date: Jun. 14, 2018

(65) Prior Publication Data
US 2020/0008555 A1    Jan. 9, 2020

(30) Foreign Application Priority Data

Dec. 9, 2016   (ES) .................................. P201631562

(51) Int. Cl.
*A45D 31/00* (2006.01)
*A45D 29/00* (2006.01)
*A61Q 3/00* (2006.01)
*C08F 2/48* (2006.01)

(52) U.S. Cl.
CPC ........... *A45D 31/00* (2013.01); *A45D 29/001* (2013.01); *A61Q 3/00* (2013.01); *A61K 2800/40* (2013.01); *C08F 2/48* (2013.01)

(58) Field of Classification Search
None
See application file for complete search history.

(56) References Cited

U.S. PATENT DOCUMENTS

2008/0031836 A1\* 2/2008 Ilekti ................... A45D 29/001
424/61

FOREIGN PATENT DOCUMENTS

DE       102013016013 A1    4/2014
WO          00076366 A1    12/2000
WO       WO-0076366 A1 \* 12/2000  ............... A61Q 3/00

OTHER PUBLICATIONS

Andrea, (How to Prep Natural Nails for gel polish application, May 21, 2015). (Year: 2015).\*

\* cited by examiner

*Primary Examiner* — Melissa S Mercier
(74) *Attorney, Agent, or Firm* — Hodgson Russ LLP

(57) ABSTRACT

The invention relates to a false nail comprising at least: one front layer (12) forming the body of the false nail (1), and a rear layer (11) of an adhesive material for attaching the body of the false nail to a natural nail. The rear layer (11) is formed by a fast-drying polymer adhesive with desiccating capacity, and the front layer (12) is made of a composite material and comprises at least a first layer (12a) of micro-hybrid composite with low contraction capacity in contact with the polymer adhesive. The invention also relates to a method for shaping the false nail on a natural nail and the use of composite material to shape same.

12 Claims, 1 Drawing Sheet

FALSE NAIL AND METHOD FOR SHAPING SAME ON A NATURAL NAIL

OBJECT OF THE INVENTION

The object of the invention comprises: a false nail and method for shaping same on a natural nail.

FIELD OF APPLICATION OF THE INVENTION

This invention applies to the fields of manicure, pedicure, podology, dermatology and, in general, any field related to the shaping of false nails or covering of natural nails.

STATE OF THE ART

The shaping of artificial nails or covering of natural nails, of both feet and hands, is currently standard practice, whether to improve aesthetics or because the nail is damaged for any reason, thus offering a protective covering.

In the case of damaged nails, covering them with a false nail to improve their aesthetics offers a protection that can entail the self-curing thereof.

At present, when a nail is damaged, techniques for applying false nails or covering using gels, acrylics or porcelain are used. Linen or silk are also used as a covering or decorative element, although they are difficult and expensive to apply.

Covering with gel and resin has certain drawbacks both from the viewpoint of application and of the result obtained from the aesthetic viewpoint.

Specifically, the gels used to cover nails have the following drawbacks:

- they have low viscosity and density, due to which they are easily damaged;
- they have low polishing capacity and can be difficult to handle;
- they have non-homogeneous density and colour, due to which the covered nail must always be painted so the false nail is not obvious;
- they have a high skin absorption rate;
- they can stain objects that come into contact with the nail;
- they need a relatively long amount of time to ensure proper drying, of approximately 5 minutes;
- to remove them they must be soaked until they go soft and, if a problem occurs, the set formed by the nail and the gel cover must be detached.

The incorrect use of acrylics can stunt nail growth. Furthermore, acrylics require chemical polymerisation (hardening) and that makes them difficult to handle, since two components must be mixed; said mixture generates the entrance of air in the dough and, therefore, the presence of porosities. In addition to having to add a reaction time (3 to 5 minutes), another drawback, which explains the change in trend towards gel nails, is a strong acrylic smell both during application and removal for 20 minutes in acetone. The final result is an unstable product in terms of properties.

Gel nails (oligomers), which are usually applied on the acrylic to reduce their porosity and offer a shinier final appearance, require exposure to UV rays to harden (spectrum of frequency closest to x-rays) and can cause burns on skin due to its prolonged exposure (3 to 5 minutes). Gels can also be applied on a plastic medium previously attached to the nail surface; but this adhesive has the drawback that in case of accident it will tear off the natural nail to which it is adhered. Removing it requires long and painstaking filing. And it must be painted with nail polish so the false nail is not obvious.

The use of resin to attach gel nails also has its drawbacks, such as: it is very uncomfortable to work with, since it contains ethanols which cause dizziness; it requires a relatively long drying time (3 to 4 minutes) and it is a covering component.

The use of both acrylic and gel nails has contraindications to use in the case of radiotherapy, diabetes or use of antibiotics.

A process for shaping false nails on the natural nail is also known through document WO0076366A1. The process described in this document includes applying a base cover agent to the nail, subsequently laminating a photopolymerisable resin on said base cover agent, and finally proceeding to harden the resin by applying visible light rays, for example by means of a LED light source.

However, a fast-drying (less than 1 minute) base cover agent is not proposed, which will prolong the application of the method. Nor is it proposed that said agent be waterproof, due to which there is a risk of growth of bacterial colonies on the polymer adhesive layer of the nail.

Additionally, in this document the resin used is a resin lacking filler particles. This causes a high degree of contraction during polymerisation and low resistance to fracturing.

Document DE102013016013A1, wherein a photopolymerisable nail polish is described, is also known. However, in this document, said nail polish is polymerised under UV light, which is harmful, rather than visible light. Therefore, the technical problem addressed is the improvement of natural nail reconstruction and/or covering techniques using a false nail having clearly advantageous features with respect to the gel nails currently used and using a specific material that gives the body of the false nail said advantageous features.

DESCRIPTION OF THE INVENTION

The false nail that is the object of the invention, comprising a front layer that forms the body of the false nail strictly speaking, and a rear layer for attaching the body of the false nail to a natural nail, has the peculiarity that the rear layer is formed by a fast-drying polymer adhesive with desiccating capacity; and the front layer of the false nail is made of composite material and comprises at least a first layer of micro-hybrid composite, having low contraction capacity, in contact with the polymer adhesive.

The aforementioned micro-hybrid composite may be of the type used in other sectors of the art, such as in dentistry for dental reconstruction.

A person skilled in the art will know that a micro-hybrid composite consists of a mixture of resin and filler particles that enhance its properties, being typically filler particles less than or equal to 1 μm in size. In some products of this type, said particles are glass.

The use of micro-hybrid composite gives the false nail clearly advantageous features with respect to the gel nails currently used, including, namely:

- greater viscosity and density, which facilitates handling when shaping the body of the nail;
- gives the body of the nail a perfect finish, since the composite can be manufactured in a range of different colours, such that the false nail does not have to be painted;

greater hardness than the gels of current false nails and, consequently, higher polishing capacity;

very low skin absorption rates;

does not stain;

shorter hardening time than gels, approximately 20 seconds;

ease of removal, using a diamond bur;

aesthetically enhanced appearance;

and possibility of removing the body of the false composite nail in the event of any problem with the user's natural nail.

In one embodiment of the invention, the front layer of the false nail comprises a second layer of micro- or nano-hybrid liquid or pasty composite; having envisaged that said second layer may preferably be a tinted micro-hybrid pasty composite.

The composite for covering a nail, both in liquid texture and in pasty texture, may be micro- or nano-hybrid, depending on the filler loading molecule wherefrom this polymer is chemically formed; the latter have greater contraction during the photopolymerisation (hardening) thereof than the former.

Said composites may be micro-pigmented and their photopolymerisation is carried out in 20 seconds by means of a LED-type blue visible light beam.

The false nail can be regularly retouched, for example every three months depending on nail growth, using very fine-grain abrasive strips and polishing with cotton or bristle brush and applying polishing compounds.

Said false nail is removed by means of burring with diamond or ruby burs, or with nail scissors. In case of accident, the composite will break, detaching itself from the natural nail without affecting it.

Its final finish does not require colouring by means of lacquers, although it can be done without any problem in the same way as a natural nail.

In order to achieve adequate attachment of the composite body of the false nail to a natural nail of the user, instead of the resins used for attaching gel nails, the use of a polymer adhesive having a series of advantages has been envisaged, including, namely:

it is waterproof it has a shorter drying time, of approximately 20 seconds, and it is a contact product In this invention, a method for shaping the false nail of the invention on a natural nail is included, comprising the following phases:

eventually, the preparation of the surface of the nail to be covered by means of filing;

the application of a fast-drying polymer adhesive nail, with desiccating capacity, which forms a rear layer of the false nail;

the application of at least one first layer of micro-hybrid composite on the rear layer of polymer adhesive that forms part of a front layer of the false nail;

the photopolymerisation of said first layer of micro-hybrid composite;

eventually, the application of a second layer of micro- or nano-hybrid liquid or pasty composite on said first layer of micro-hybrid composite; and photocuring thereof and eventually, the finish of the front layer of the false nail by means of filing, polishing and/or superficial painting thereof.

Preferably, the polymer adhesive is left to dry for approximately 20 seconds after application to the nail before the application of the at least one first layer of micro-hybrid composite.

Preferably, the polymer adhesive will be selected such that it polymerises quickly, i.e. in less than 30 seconds, by means of photopolymerisation, under visible light. For example, under visible light applied by a LED lamp or similar. Lastly, it should be noted that another object of the invention is the use of composite material in false nails.

DESCRIPTION OF THE FIGURES

As a complement to the description being made, and for the purpose of helping to make the features of the invention more readily understandable, the present specification is accompanied by a set of drawings which, by way of illustration and not limitation, represent the following.

PREFERRED EMBODIMENT OF THE INVENTION

Figure 1A:
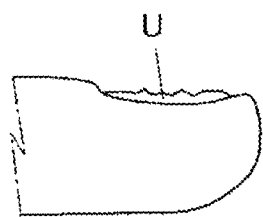
FIGS. 1a to 1e show a schematic view of successive phases of the method for covering a natural nail according to the invention, forming an artificial nail with a rear layer consisting of a fast-drying contact adhesive and a front layer of composite material constituting the body of the false nail, strictly speaking.
Figure 1B:
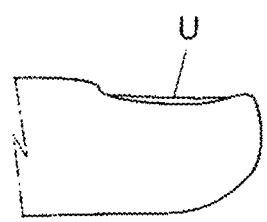
Figure 1C:
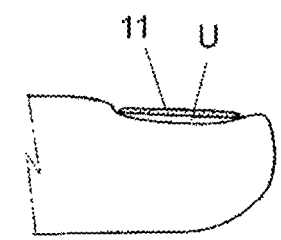
Figure 1D:
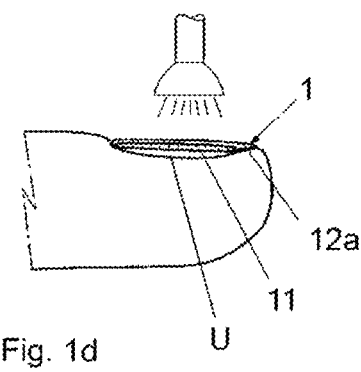
Figure 1E:
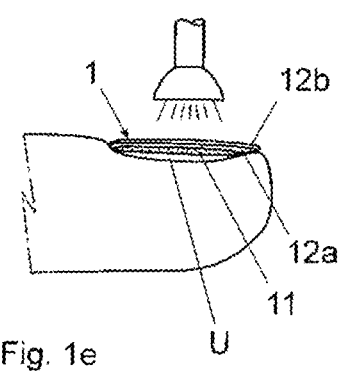

As shown in the attached figures, shaping the false nail of the invention on a natural nail, shown in FIG. 1a, and covering said natural nail (U) involves the following operations: the surface of the nail (U) to be covered is firstly prepared by filing, defining an adequate surface therein to initiate the covering as shown in FIG. 1b; next, a fast-drying polymer adhesive with desiccating capacity that polymerises under the effect of visible light is applied to the nail (U) and forms a rear layer (11) of the false nail as shown in the FIG. (1c); next, a first layer (12a) of micro-hybrid composite that forms part of a front layer (12) of the false nail (1) is applied over the rear layer (11) of polymer adhesive, prior to photopolymerising said first layer (12a) of composite material (FIG. 1d), next, as shown in FIG. 1d), a second layer (12b) of micro- or nano-hybrid liquid composite is applied over said first layer (12a); and it is photopolymerised.

Lastly, the front layer (12) of the false nail (1) is finished by filing, polishing and/or surface painting in order to enhance its aesthetic finish.

In this example of embodiment the polymer adhesive, used firstly on the nail or nail bed to form the rear layer (11), is a polymer adhesive with amelodentinal features, an aromatic diacrylate containing benzene groups mixed with an aliphatic diacrylate, which liquidises it, and hydrophilic molecules. This polymer adhesive can be photopolymerised (5 seconds) under visible light, or not, and has high desiccating capacity.

The first layer (12a) of the front layer is a micro-hybrid pasty composite (less contraction capacity, less effect on the action of the adhesive) and the second layer (12b) is a nano-hybrid liquid composite, photocured in 20 seconds.

Depending on the nail texture to be obtained, in the two applications with composite forming the front layer (12) of the false nail, the composite can be compacted by compressing it with PVC tape while being photopolymerised.

Figure 2:
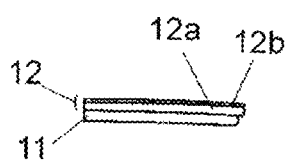
FIG. 2 shows a cross-sectional view of a false nail according to the invention.

The false nail (1) obtained and schematically represented on its own in FIG. 2 comprises a rear layer (11) of adhesive and a front layer (12) of composite material that form the body of the false nail (1) and consists of a first layer (12a) and a second layer (12b) of composite material.

Having sufficiently described the nature of the invention, in addition to a preferred example of embodiment, it is hereby stated for the relevant purposes that the materials, shape, size and arrangement of the described elements can be modified, provided that it does not involve an alteration of the essential features of the invention claimed below.

The invention claimed is:

1. A false nail, comprising: a front layer (12) forming a body of the false nail (1) and a rear layer (11) of an adhesive material for attaching the body of the false nail to a natural nail, wherein the adhesive material comprises a waterproof polymer adhesive having a desiccating capacity and being photopolymerisable; and wherein the front layer (12) of the false nail (1) comprises a composite material including a first layer (12a) of micro-hybrid composite with low contraction capacity in contact with the waterproof polymer adhesive.

2. The false nail according to claim 1, wherein the composite material further includes a second layer (12b) comprising a liquid micro-hybrid composite or a pasty micro-hybrid composite.

3. The false nail according to claim 1, wherein the composite material further includes a second layer (12b) comprising a tinted pasty micro-hybrid composite.

4. The false nail according to claim 1, wherein the waterproof polymer adhesive is a mixture of an aromatic diacrylate containing benzene groups and an aliphatic diacrylate.

5. The false nail according to claim 1, wherein the waterproof polymer adhesive has a drying time of approximately 20 seconds.

6. The false nail according to claim 1, wherein the micro-hybrid composite is photopolymerisable.

7. A method for shaping a false nail on a natural nail, comprising:
   applying a waterproof polymer adhesive on the natural nail (U), with desiccating capacity and being photopolymerisable, which forms a rear layer (11) of the false nail (1);
   applying at least one first layer (12a) of a micro-hybrid composite on the rear layer (11) of the waterproof polymer adhesive to form part of a front layer (12) of the false nail (1); and
   photopolymerizing said first layer (12a) of composite material.

8. The method of claim 7, further comprising preparing a surface of the natural nail (U) to be covered by filing.

9. The method of claim 7, further comprising:
   applying a second layer (12b) of a liquid micro-hybrid composite or a pasty micro-hybrid composite to said first layer (12a); and
   photocuring said second layer (12b).

10. The method of claim 7, further comprising finishing the front layer (12) by filing, polishing and/or surface painting thereof.

11. The method of claim 7, further comprising drying the waterproof polymer adhesive for at least 20 seconds after application on the nail (U) prior to applying the at least one first layer (12a) of micro-hybrid composite.

12. The method of claim 7, wherein the waterproof polymer adhesive is a mixture of an aromatic diacrylate containing benzene groups and an aliphatic diacrylate.

* * * * *